United States Patent [19]

Olsen et al.

[11] Patent Number: 5,635,616
[45] Date of Patent: Jun. 3, 1997

[54] HUMAN OXALYL-COA DECARBOXYLASE

[75] Inventors: Henrik S. Olsen; Timothy A. Coleman, both of Gaithersburg; Mark D. Adams, North Potomac, all of Md.

[73] Assignees: Human Genome Sciences, Inc.; The Institute for Genomic Res., both of Md.

[21] Appl. No.: 458,120

[22] Filed: Jun. 2, 1995

[51] Int. Cl.$^6$ .......................... C07H 21/02; C07H 21/04; C12Q 1/68; C12P 21/04
[52] U.S. Cl. .................. 536/23.1; 435/6; 435/70.3; 435/91.41; 435/348; 435/325; 435/358; 435/365; 435/419; 435/357; 435/367
[58] Field of Search .................. 536/23.1; 435/69.1, 435/6, 240.2, 252.3, 183, 232, 70.1, 71.1, 70.3

[56] References Cited

U.S. PATENT DOCUMENTS 5,547,870   8/1996   Datta et al. .................. 435/240.4

FOREIGN PATENT DOCUMENTS

| | | | |
|---|---|---|---|
| WO88/08450 | 11/1988 | WIPO | C12N 7/00 |
| WO95/31537 | 11/1995 | WIPO | C12N 9/88 |
| WO95/35377 | 12/1995 | WIPO | C12N 15/31 |

OTHER PUBLICATIONS

Blackmore, et al., *Biochem J.*, (1970) 118, 53–59.
Baetz, et al., *Journal of Bacteriology*, May 1989, pp. 2605–2608, vol. 171, No. 5.
Lung, et al., *Journal of Bacteriology*, Apr. 1994, pp. 2468–2472, vol. 176, No. 8.
Lung, et al., *American Journal of Kidney Diseases*, vol. XVII, No. 4 (Apr.), 1991; pp. 381–385.
Mehta, et al., *The Journal of Biological Chemistry*, vol. 266, No. 35, Issue of Dec. 15, pp. 23548–23553, 1991.
Allison, M., et al., Arch Microbiol, 141:1–7 (1985).
Triebig, et al., *Clinica Chimica Acta.*, 108 (1980) 355–360.
Chemical Abstracts, vol. 118, No. 15, p. 406 (Apr. 12, 1993).
Quayle, J. R. (1969) Methods in Enzymology 13:369–372.

*Primary Examiner*—W. Gary Jones
*Assistant Examiner*—Amy Atzel
*Attorney, Agent, or Firm*—Elliot M. Olstein; J. G. Mullins

[57] ABSTRACT

A human oxalyl-CoA decarboxylase polypeptide and DNA (RNA) encoding such polypeptide and a procedure for producing such polypeptide by recombinant techniques and for producing an antibody against such polypeptide are disclosed. Also disclosed is a combination of the polypeptide of the present invention and a suitable pharmaceutical carrier for providing a therapeutically effective amount of the polypeptide for the treatment of urolithiasis and hyperoxaluria. Also disclosed are assays for identifying mutations in nucleic acid sequence encoding a polypeptide of the present invention and for detecting altered levels of the polypeptide of the present invention.

22 Claims, 7 Drawing Sheets

FIG. 1A

```
CGGTGGAAGATGCCGGACAGTAACTTCGCAGAGCGCAGCGAGGAGCAGGTGTCTGGTGCT
----+----|----+----|----+----|----+----|----+----|----+----|
            MetProAspSerAsnPheAlaGluArgSerGluGlnValSerGlyAla

AAAGTCATCGCTCAGGCCCTGAAAAACGCAAGATGTGGAGTACATATTTGGCATCGTAGGC
----+----|----+----|----+----|----+----|----+----|----+----|
LysValIleAlaGlnAlaLeuLysThrGlnAspValGluTyrIlePheGlyIleValGly

ATCCCAGTGACCGAAATCGGCCATTGCTGCCCAGCAGCTAGGCATCAAGTACATCGGGATG
----+----|----+----|----+----|----+----|----+----|----+----|
IleProValThrGluIleAlaIleAlaAlaAlaGlnLeuGlyIleLysTyrIleGlyMet

AGGAATGAGCAAGCGGCTTGTTATGCTGCCTCCGCGATTGGATATCTGACAAGCAGGCCA
----+----|----+----|----+----|----+----|----+----|----+----|
ArgAsnGluGlnAlaAlaCysTyrAlaAlaSerAlaIleGlyTyrLeuThrSerArgPro

GGAGTCTGCCTTGTTGTTTCTGGCCCAGGTCTCATCCATGCCCTTGGGCGGTATGGCAAAT
----+----|----+----|----+----|----+----|----+----|----+----|
GlyValCysLeuValValSerGlyProGlyLeuIleHisAlaLeuGlyMetAlaAsn
```

FIG. 1B

```
GCAAACATGAACTGCTGGCCCTTGCTTGTGATTGGTGGTTCCCTCTGAAAGAAACCAAGAA
----+----+----+----+----+----+----+----+----+----+----+----+
 AlaAsnMetAsnCysTrpProLeuLeuValIleGlyGlySerSerGluArgAsnGlnGlu

ACAATGGGAGCTTTCCTCCAGGAGTTCCTCCAGGTTGAAGCTTGTAGATTATATACCAAGTTC
----+----+----+----+----+----+----+----+----+----+----+----+
 ThrMetGlyAlaPheGlnGluPheProGlnValGluAlaCysArgLeuTyrThrLysPhe

TCTGCCCGCCCAAGCAGCATAGAAGCTATTCCTTTGTTATTGAAAAGGCAGTGAGAAGC
----+----+----+----+----+----+----+----+----+----+----+----+
 SerAlaArgProSerSerIleGluAlaIleProPheValIleGluLysAlaValArgSer

AGTATCTATGGTCGTCCAGGTGCTTGCTATGTTGACATACCAGCAGATTTGTGAACCTT
----+----+----+----+----+----+----+----+----+----+----+----+
 SerIleTyrGlyArgProGlyAlaCysTyrValAspIleProAlaAspPheValAsnLeu

CAGGTGAATGTGAATTCTATAAAGTACATGGAACGCTGCATGTCACCTCCTATTAGCATG
----+----+----+----+----+----+----+----+----+----+----+----+
 GlnValAsnValAsnSerIleLysTyrMetGluArgCysMetSerProProIleSerMet
```

FIG. 1C

```
GCAGAAACCTCTGCTGTGTGCACGGGCGGCTTCTGTTATTAGGAATGCCAAACAACCCCTT
--------+---------+---------+---------+---------+---------+
AlaGluThrSerAlaValCysThrAlaAlaSerValIleArgAsnAlaLysGlnProLeu

CTTATCATCGGGAAAGGTGCTGCTTACGCTCATGCAGAAGAGAGTATCAAGAAATTGGTG
--------+---------+---------+---------+---------+---------+
LeuIleIleGlyLysGlyAlaAlaTyrAlaAlaHisAlaGluGluSerIleLysLysLeuVal

GAGCAATATAAACTGCCATTTTTGCCCACCCCTATGGGGAAGGGTGTTGTCCCTGACAAT
--------+---------+---------+---------+---------+---------+
GluGlnTyrLysLeuProPheLeuProThrProMetGlyLysGlyValValProAspAsn

CATCCATACTGTGTAGGTGCAGCCAGATCCAGGGCTTTGCAATTTGCTGATGTAATTGTG
--------+---------+---------+---------+---------+---------+
HisProTyrCysValGlyAlaAlaArgSerArgAlaLeuGlnPheAlaAspValIleVal

TTATTTGGTGCCAGACTAAATTGGATTTTACATTTTGGACTGCCTCCAAGATATCAGCCA
--------+---------+---------+---------+---------+---------+
LeuPheGlyAlaArgLeuAsnTrpIleLeuHisPheGlyLeuProProArgTyrGlnPro
```

FIG. 1D

```
GATGTGAAGTTTATCCAGGTTGATATCTGTGCAGAAGAATTGGGAATAATGTAAAGCCC
----------+---------+---------+---------+---------+---------+
 AspValLysPheIleGlnValAspIleCysAlaGluGluLeuGlyAsnAsnValLysPro

GCTGTTACTTTGCTAGGAAACATACATGCTGTCACTAAGCAGCTTTTAGAGGAACTTGAT
----------+---------+---------+---------+---------+---------+
 AlaValThrLeuLeuGlyAsnIleHisAlaValThrLysGlnLeuLeuGluGluLeuAsp

AAAACACCATGGCAGTATCCTCCAGAGAGCAAGTGGTGAAAACTCTGAGAGAAAAAATG
----------+---------+---------+---------+---------+---------+
 LysThrProTrpGlnTyrProProGluSerLysTrpTrpLysThrLeuArgGluLysMet

AAGAGCAATGAAGCTGCATCCAAGGAACTAGCTTCTAAAAAATCCCTGCCTATGAATTAT
----------+---------+---------+---------+---------+---------+
 LysSerAsnGluAlaAlaSerLysGluLeuAlaSerLysLysSerLeuProMetAsnTyr

TACACAGTATTCTACCATGTTCAAGAACAACTACCTAGAGACTGTTTCGTGGTAAGTGAA
----------+---------+---------+---------+---------+---------+
 TyrThrValPheTyrHisValGlnGluGlnLeuProArgAspCysPheValValSerGlu
```

FIG. 1E

```
GGAGCAAATACTATGGACATTGGGACGGACTGTGCTTCAGAACTACCTTCCTCGTCACAGG
----+---------+---------+---------+---------+---------+
   GlyAlaAsnThrMetAspIleGlyArgThrValLeuGlnAsnTyrLeuProArgHisArg

CTTGATGCTGGTACTTTCGGAACAATGGGAGTTGGTTTGGGATTTGCTATTGCAGCTGCC
----+---------+---------+---------+---------+---------+
   LeuAspAlaGlyThrPheGlyThrMetGlyValGlyLeuGlyPheAlaIleAlaAlaAla

GTGGTGGCTAAAGATAGAAGCCCTGGGCAATGGATCATCTGTGTGGAAGGAGACAGTGCA
----+---------+---------+---------+---------+---------+
   ValValAlaLysAspArgSerProGlyGlnTrpIleIleCysValGluGlyAspSerAla

TTTGGGTTTTCTGGCATGGAGGTAGAAACCATCTGCAGTACAACTTGCCAATCATACTG
----+---------+---------+---------+---------+---------+
   PheGlyPheSerGlyMetGluValGluThrIleCysArgTyrAsnLeuProIleIleLeu

TTGGTAGTGAATAACAATGGAATTTACCAAGGTTTTGATACAGATACTTGGAAAGAAATG
----+---------+---------+---------+---------+---------+
   LeuValValAsnAsnGlyIleTyrGlnGlyPheAspThrAspThrTrpLysGluMet

TTAAAATTTCAAGATGCTACTGCAGTGGTCCCTCCAATGTGTTTGCTGCCAAATTCACAT
----+---------+---------+---------+---------+---------+
   LeuLysPheGlnAspAlaThrAlaValValProProMetCysLeuLeuProAsnSerHis
```

FIG. 2A

```
          10         20         30         40         50
          MSNDDNVELTDGFHVLIDALKMNDIDTMYGVVGIPITNLARMWQDDGQRFYSF
          :|   ::  |:: |||  :|::|||  :| | |:: |:  ||  ::
          MPDSNFAERSEEQVSGAKVIAQALKTQDVEYIFGIVPVTELAIAAQQLGIKYIGM
          60         70         80         90        100        110

RHEQHAGYAASIAGYIEGKPGVCLTVSAPGFLNGVTSLAHATTNCFPMILLSGSSEREIV
:||| ||||||| ||  :| |||| ||| |||:|:|:|:|  | |:|||:||||||:|
RNEQAACYAASAIGYLTSRPGVCLVVSGPGLIHALGGMANAMNCWPLLIGGSSERNQE
           120        130        140        150        160        170

DLQQGDYEEMDQMNVARPHCKASFRINSIKDIPIGIARAVRTAVSGRPGGVYVDLPAKLF
:: ||: |:| |  |:  |  | | |:  |:  ||||:  |   |||| ||:|||:|||
TM--GAFQEFPQVEACRLYTKFSARPSSIEAIPFVIEKAVRSSIYGRPGACYVDIPADFV
              180        190        200        210        220        230

GQTISVEEANKLLFKPIDPAPAQIPAEDALARAADLIKNARPVIMLGKGAAYAQCDDEI
 ::| :| : ::|:|  ::|:: |  :|||: |||:|||| ||||||||||||  |::|
NLQVNV-NSIKYMERCMSP-PISMAETSAVCTAASVIRNAKQPLLIIGKGAAYAHAEESI
              240        250        260        270        280        290

RALVEETGIPFLPMGMAKGLLPDNHPQSAAATRAFALAQCDVCVLIGARLNWLMQHGKGK
:||| |: ::| |  ||| ||||||||: |||:||| | ||||:|||||||:| |:|  
KKLVEQYKLPFLPTPMGKGVVPDNHPYCVGAARSRALQFADVIVLFGARLNWILHFGLPP
```

FIG. 2B

```
        300         310         320         330         340         350
TWGDELKKYVQIDIQANEMDSNQPIAAPVVGDIKSAVSLLRKALKGAP---KADAEWTGA  :
 : :: ||||| |:|:  ::|||| |:::|:: |  : ::    ::::  |         :
RYQPDV-KFIQVDICAEELGNNVKPAVTLLGNIHAVTKQLLEELDKTPWQYPPESKWWKT
        360         370         380         390         400         410
LKAKVDGNKAKLAGKMTAETPSGMNYSNSLGVVRDFMLANPDISLVNEGANALDNTRMI
|:::||   || ||   |:  ||| ::  |||  :  :  :|:||   :  :|
LREKMKSNEA--ASKELASKKSLPMNYYTVFYHVQEQL---PRDCFVVSEGANTMDIGRTV
        420         430         440         450         460
VDMLKPRKRLDSGTWGVMGIGMGYCVAAAAVT------GKPVIAVEGDSAFGFSGMELETI
 ::   |||||||:|||||:|:|:: ::|:|:      |:| :| |||||||||||||||
LQNYLPRHRLDAGTFGTMGVGLGFAIAAAVVAKDRSPGQWIICVEGDSAFGFSGMEVETI
        470         480         490         500         510
CRYNLPVTVIIMNNGGIYKGNEADP--------QPGVIS--CTRLTRGRYDMMMEAFGG
|||||| :|: ::|||||:  :  :        :: |: :  | |  | ::|:||||||
CRYNLPIILLVVNNGGIYQGFDTDTWKEMLKFQDATAVVPPMCL-LPNSHYEQVMTAFGG
        520         530         540         550         560
KGYVANTPAELKAALEEAVA-SGKPCLINAMIDPDAGVESGRIKSLNVVSKVGKK
|||  : |||||:| ||: | : |||:|::| ||: ::|||||||:|| ::|
KGYFVQTPEELQKSLRQSLADTTKPSLINIMIEPQATRKAQDFHWLTRSNM
```

HUMAN OXALYL-COA DECARBOXYLASE

This invention relates to newly identified polynucleotides, polypeptides encoded by such polynucleotides, the use of such polynucleotides and polypeptides, as well as the production of such polynucleotides and polypeptides. More particularly, the polypeptide of the present invention is human Oxalyl-CoA Decarboxylase.

Evidence suggests that the formation of calcium-oxalate stones in the urine is dependent on the saturation levels of both calcium and oxalate, thus, management of one or both of these ions in individuals susceptible to stone formation in the urinary tract (urolithiasis) appears important. Urolithiasis is a common urinary tract problem afflicting more than 10% of the U.S. population (Sierakowski, R. et al., Invest. Urol., 15:438–441 (1978)). Urinary tract stones are usually classified according to their composition, with the most frequently encountered (70%) being the calcium stone which is composed of calcium oxalate alone or calcium oxalate mixed with calcium phosphate. Although precipitation of calcium oxalate depends on a urine saturated with both calcium and oxalate ions in a meta-stable state, it has been argued that the oxalate ion concentration is more significant in the formation of urinary calcium oxalate stones.

The majority of oxalate in plasma and urine is derived from the endogenous metabolism of ascorbic acid, glyoxylate, and to a lesser degree, tryptophan (Nath, R. et al., Pergamon Press, pp. 55–58 (1984)). In addition, between 10% and 20% of the urinary oxalate is absorbed from the diet, especially through ingestion of leafy vegetables and plant materials. Fortunately, most dietary oxalate appears to be bound by intraluminal calcium and is excreted as an insoluble salt. Thus, there is an inverse relationship between ingested calcium and absorbed oxalate. (Ernest, D. L., et al., Gastroenterology, 66:1114–1122 (1964)).

Either abnormal synthesis or hyper-absorption of oxalate can lead to a serious condition referred to as hyperoxaluria (Liedtke, R. R. et al., Urol. Res., 16:188–189 (1988)). Although this condition may have a genetic basis, the vast majority of cases remain idiopathic (Nath, R. et al., Pergamon Press, pp. 55–58 (1984)). Whether the underlying cause is a disturbance in calcium metabolism or merely increased levels of oxalate there is a strong association between increased levels of urinary oxalate and calcium oxalate stone disease in man.

The basis of stone formation in the urinary tract and ways to treat this disorder has recently been the subject of intensive study. A plant-derived oxalyl-CoA decarboxylase gene has been inserted into human cells as a means of lowering plasma and urinary oxalate concentrations. The oxalyl-CoA decarboxylase gene has been cloned from bacterium *Oxalobacer formigenes*. Lung, H. Y. et al., Am. J. Kidney Dis., 17:381–5 (1991).

Accordingly, an enzyme that lowers the oxalate levels in the plasma, and subsequently the urine, would decrease the incidence of calcium oxalate stone formation.

In accordance with one aspect of the present invention, there is provided a novel mature polypeptide, as well as biologically active and diagnostically or therapeutically useful fragments, analogs and derivatives thereof. The polypeptide of the present invention is of human origin.

In accordance with another aspect of the present invention, there are provided isolated nucleic acid molecules encoding a polypeptide of the present invention including mRNAs, DNAs, cDNAs, genomic DNAs as well as analogs and biologically active and diagnostically or therapeutically useful fragments thereof.

In accordance with yet a further aspect of the present invention, there is provided a process for producing such polypeptide by recombinant techniques comprising culturing recombinant prokaryotic and/or eukaryotic host cells, containing a nucleic acid sequence encoding a polypeptide of the present invention, under conditions promoting expression of said protein and subsequent recovery of said protein.

In accordance with yet a further aspect of the present invention, there is provided a process for utilizing such polypeptide, or polynucleotide encoding such polypeptide for therapeutic purposes, for example, preventing calcium-oxalate stone formation and hyperoxaluria.

In accordance with yet a further aspect of the present invention, there is also provided nucleic acid probes comprising nucleic acid molecules of sufficient length to specifically hybridize to a nucleic acid sequence of the present invention.

In accordance with yet a further aspect of the present invention, there are provided antibodies against such polypeptides.

In accordance with still another aspect of the present invention, there are provided diagnostic assays for detecting diseases or susceptibility to diseases related to mutations in the nucleic acid sequences encoding a polypeptide of the present invention.

In accordance with yet a further aspect of the present invention, there is provided a process for utilizing such polypeptides, or polynucleotides encoding such polypeptides, for in vitro purposes related to scientific research, for example, synthesis of DNA and manufacture of DNA vectors.

These and other aspects of the present invention should be apparent to those skilled in the art from the teachings herein.

BRIEF DESCRIPTION OF THE DRAWINGS

The following drawings are illustrative of embodiments of the invention and are not meant to limit the scope of the invention as encompassed by the claims.

FIG. 1 displays the cDNA sequence and corresponding deduced amino acid sequence of the mature oxalyl-CoA decarboxylase polypeptide. The standard three letter abbreviation for amino acids is used.

FIG. 2 is an amino acid sequence comparison between oxalyl-CoA decarboxylase from the bacterium *Oxalobacter formigenes* (upper line) and the polypeptide encoded by the polynucleotide sequence of the present invention (lower line).

In accordance with an aspect of the present invention, there is provided an isolated nucleic acid (polynucleotide) which encodes for the mature polypeptide having the deduced amino acid sequence of FIG. 1 (SEQ ID NO:2) or for the mature polypeptide encoded by the cDNA of the clone deposited as ATCC Deposit No. 75715 on Mar. 18, 1994.

The ATCC number referred to above is directed to a biological deposit with the ATCC, 12301 Parklawn Drive, Rockville, Md. 20852. Since the strain referred to is being maintained under the terms of the Budapest Treaty, it will be made available to a patent office signatory to the Budapest Treaty.

The polynucleotide of this invention was discovered in a cDNA library derived from the human pancreas. It contains an open reading frame encoding a mature protein of 578 amino acid residues. The protein of the present invention is approximately 50–60% homologous to the oxalyl-CoA Decarboxylase from the bacterium *Oxalobacer formigenes* at the amino acid level. The homology starts at amino acid 8 of the bacterial enzyme (see FIG. 2).

The polynucleotide of the present invention may be in the form of RNA or in the form of DNA, which DNA includes cDNA, genomic DNA, and synthetic DNA. The DNA may be double-stranded or single-stranded, and if single stranded may be the coding strand or non-coding (anti-sense) strand. The coding sequence which encodes the mature polypeptide may be identical to the coding sequence shown in FIG. 1 (SEQ ID NO:1) or that of the deposited clone or may be a different coding sequence which coding sequence, as a result of the redundancy or degeneracy of the genetic code, encodes the same mature polypeptide as the DNA of FIG. 1 (SEQ ID NO:1) or the deposited cDNA.

The polynucleotide which encodes for the mature polypeptide of FIG. 1 (SEQ ID NO:2) or for the mature polypeptide encoded by the deposited cDNA may include, but is not limited to: only the coding sequence for the mature polypeptide; the coding sequence for the mature polypeptide and additional coding sequence; the coding sequence for the mature polypeptide (and optionally additional coding sequence) and non-coding sequence, such as introns or non-coding sequence 5' and/or 3' of the coding sequence for the mature polypeptide.

Thus, the term "polynucleotide encoding a polypeptide" encompasses a polynucleotide which includes only coding sequence for the polypeptide as well as a polynucleotide which includes additional coding and/or non-coding sequence.

The present invention further relates to variants of the hereinabove described polynucleotides which encode for fragments, analogs and derivatives of the polypeptide having the deduced amino acid sequence of FIG. 1 (SEQ ID NO:2) or the polypeptide encoded by the cDNA of the deposited clone. The variant of the polynucleotide may be a naturally occurring allelic variant of the polynucleotide or a non-naturally occurring variant of the polynucleotide.

Thus, the present invention includes polynucleotides encoding the same mature polypeptide as shown in FIG. 1 (SEQ ID NO:2) or the same mature polypeptide encoded by the cDNA of the deposited clone as well as variants of such polynucleotides which variants encode for a fragment, derivative or analog of the polypeptide of FIG. 1 (SEQ ID NO:2) or the polypeptide encoded by the cDNA of the deposited clone. Such nucleotide variants include deletion variants, substitution variants and addition or insertion variants.

As hereinabove indicated, the polynucleotide may have a coding sequence which is a naturally occurring allelic variant of the coding sequence shown in FIG. 1 (SEQ ID NO:1) or of the coding sequence of the deposited clone. As known in the art, an allelic variant is an alternate form of a polynucleotide sequence which may have a substitution, deletion or addition of one or more nucleotides, which does not substantially alter the function of the encoded polypeptide.

The polynucleotides of the present invention may also have the coding sequence fused in frame to a marker sequence which allows for purification of the polypeptide of the present invention. The marker sequence may be a hexa-histidine tag supplied by a pQE-9 vector to provide for purification of the mature polypeptide fused to the marker in the case of a bacterial host, or, for example, the marker sequence may be a hemagglutinin (HA) tag when a mammalian host, e.g. COS-7 cells, is used. The HA tag corresponds to an epitope derived from the influenza hemagglutinin protein (Wilson, I., et al., Cell, 37:767 (1984)).

The term "gene" means the segment of DNA involved in producing a polypeptide chain; it includes regions preceding and following the coding region (leader and trailer) as well as intervening sequences (introns) between individual coding segments (exons).

Fragments of the full length oxalyl-CoA decarboxylase gene may be used as a hybridization probe for a cDNA library to isolate the full length gene and to isolate other genes which have a high sequence similarity to the gene or similar biological activity. Probes of this type preferably have at least 30 bases and may contain, for example, 50 or more bases. The probe may also be used to identify a cDNA clone corresponding to a full length transcript and a genomic clone or clones that contain the complete gene including regulatory and promotor regions, exons, and introns. An example of a screen comprises isolating the coding region of the gene by using the known DNA sequence to synthesize an oligonucleotide probe. Labeled oligonucleotides having a sequence complementary to that of the gene of the present invention are used to screen a library of human cDNA, genomic DNA or mRNA to determine which members of the library the probe hybridizes to.

The present invention further relates to polynucleotides which hybridize to the hereinabove-described sequences if there is at least 70%, preferably at least 90%, and more preferably at least 95% identity between the sequences. The present invention particularly relates to polynucleotides which hybridize under stringent conditions to the hereinabove-described polynucleotides. As herein used, the term "stringent conditions" means hybridization will occur only if there is at least 95% and preferably at least 97% identity between the sequences. The polynucleotides which hybridize to the hereinabove described polynucleotides in a preferred embodiment encode polypeptides which either retain substantially the same biological function or activity as the mature polypeptide encoded by the cDNAs of FIG. 1 (SEQ ID NO:1) or the deposited cDNA(s).

Alternatively, the polynucleotide may have at least 20 bases, preferably 30 bases, and more preferably at least 50 bases which hybridize to a polynucleotide of the present invention and which has an identity thereto, as hereinabove described, and which may or may not retain activity. For example, such polynucleotides may be employed as probes for the polynucleotide of SEQ ID NO:1, for example, for recovery of the polynucleotide or as a diagnostic probe or as a PCR primer.

Thus, the present invention is directed to polynucleotides having at least a 70% identity, preferably at least 90% and more preferably at least a 95% identity to a polynucleotide which encodes the polypeptide of SEQ ID NO:2 as well as fragments thereof, which fragments have at least 30 bases and preferably at least 50 bases and to polypeptides encoded by such polynucleotides.

The deposit(s) referred to herein will be maintained under the terms of the Budapest Treaty on the International Recognition of the Deposit of Micro-organisms for purposes of Patent Procedure. These deposits are provided merely as convenience to those of skill in the art and are not an admission that a deposit is required under 35 U.S.C. §112. The sequence of the polynucleotides contained in the deposited materials, as well as the amino acid sequence of the polypeptides encoded thereby, are incorporated herein by reference and are controlling in the event of any conflict with any description of sequences herein. A license may be required to make, use or sell the deposited materials, and no such license is hereby granted.

The present invention further relates to a polypeptide which has the deduced amino acid sequence of FIG. 1 (SEQ ID NO:2) or which has the amino acid sequence encoded by the deposited cDNA, as well as fragments, analogs and derivatives of such polypeptide.

The terms "fragment," "derivative" and "analog" when referring to the polypeptide of FIG. 1 (SEQ ID NO:2) or that encoded by the deposited cDNA, means a polypeptide which retains essentially the same biological function or activity as such polypeptide. Thus, an analog includes a proprotein which can be activated by cleavage of the proprotein portion to produce an active mature polypeptide.

The polypeptide of the present invention may be a recombinant polypeptide, a natural polypeptide or a synthetic polypeptide, preferably a recombinant polypeptide.

The fragment, derivative or analog of the polypeptide of FIG. 1 (SEQ ID NO:2) or that encoded by the deposited cDNA may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide. Such fragments, derivatives and analogs are deemed to be within the scope of those skilled in the art from the teachings herein.

The polypeptides and polynucleotides of the present invention are preferably provided in an isolated form, and preferably are purified to homogeneity.

The term "isolated" means that the material is removed from its original environment (e.g., the natural environment if it is naturally occurring). For example, a naturally-occurring polynucleotide or polypeptide present in a living animal is not isolated, but the same polynucleotide or polypeptide, separated from some or all of the coexisting materials in the natural system, is isolated. Such polynucleotides could be part of a vector and/or such polynucleotides or polypeptides could be part of a composition, and still be isolated in that such vector or composition is not part of its natural environment.

The polypeptides of the present invention include the polypeptide of SEQ ID NO:2 (in particular the mature polypeptide) as well as polypeptides which have at least 70% similarity (preferably a 70% identity) to the polypeptide of SEQ ID NO:2 and more preferably at least a 90% similarity (more preferably at least a 90% identity) to the polypeptide of SEQ ID NO:2 and still more preferably at least a 95% similarity (still more preferably at least a 95% identity) to the polypeptide of SEQ ID NO:2 and also include portions of such polypeptides with such portion of the polypeptide generally containing at least 30 amino acids and more preferably at least 50 amino acids.

As known in the art "similarity" between two polypeptides is determined by comparing the amino acid sequence and its conserved amino acid substitutes of one polypeptide to the sequence of a second polypeptide.

Fragments or portions of the polypeptides of the present invention may be employed for producing the corresponding full-length polypeptide by peptide synthesis; therefore, the fragments may be employed as intermediates for producing the full-length polypeptides. Fragments or portions of the polynucleotides of the present invention may be used to synthesize full-length polynucleotides of the present invention.

The present invention also relates to vectors which include polynucleotides of the present invention, host cells which are genetically engineered with vectors of the invention and the production of polypeptides of the invention by recombinant techniques.

Host cells are genetically engineered (transduced or transformed or transfected) with the vectors of this invention which may be, for example, a cloning vector or an expression vector. The vector may be, for example, in the form of a plasmid, a viral particle, a phage, etc. The engineered host cells can be cultured in conventional nutrient media modified as appropriate for activating promoters, selecting transformants or amplifying the genes of the present invention. The culture conditions, such as temperature, pH and the like, are those previously used with the host cell selected for expression, and will be apparent to the ordinarily skilled artisan.

The polynucleotides of the present invention may be employed for producing polypeptides by recombinant techniques. Thus, for example, the polynucleotide may be included in any one of a variety of expression vectors for expressing a polypeptide. Such vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, and pseudorabies. However, any other vector may be used as long as it is replicable and viable in the host.

The appropriate DNA sequence may be inserted into the vector by a variety of procedures. In general, the DNA sequence is inserted into an appropriate restriction endonuclease site(s) by procedures known in the art. Such procedures and others are deemed to be within the scope of those skilled in the art.

The DNA sequence in the expression vector is operatively linked to an appropriate expression control sequence(s) (promoter) to direct mRNA synthesis. As representative examples of such promoters, there may be mentioned: LTR or SV40 promoter, the E. coli. lac or trp, the phage lambda $P_L$ promoter and other promoters known to control expression of genes in prokaryotic or eukaryotic cells or their viruses. The expression vector also contains a ribosome binding site for translation initiation and a transcription terminator. The vector may also include appropriate sequences for amplifying expression.

In addition, the expression vectors preferably contain one or more selectable marker genes to provide a phenotypic trait for selection of transformed host cells such as dihydrofolate reductase or neomycin resistance for eukaryotic cell culture, or such as tetracycline or ampicillin resistance in E. coli.

The vector containing the appropriate DNA sequence as hereinabove described, as well as an appropriate promoter or control sequence, may be employed to transforman appropriate host to permit the host to express the protein.

As representative examples of appropriate hosts, there may be mentioned: bacterial cells, such as E. coli, Streptomyces, Salmonella typhimurium; fungal cells, such as yeast; insect cells such as Drosophila S2 and Spodoptera Sf9; animal cells such as CHO, COS or Bowes melanoma; adenoviruses; plant cells, etc. The selection of an appropriate host is deemed to be within the scope of those skilled in the art from the teachings herein.

More particularly, the present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available. The following vectors are provided by way of example; Bacterial: pQE70, pQE60, pQE-9 (Qiagen), pBS, pD10, phagescript, psiX174, pbluescript SK, pbsks, pNH8A, pNH16a, pNH18A, pNH46A (Stratagens); ptrc99a, pKK223-3, pKK233-3, pDR540, pRIT5 (Pharmacia); Eukaryotic: pWLNEO, pSV2CAT, pOG44, pXT1, pSG (Stratagene) pSVK3, pBPV, pMSG, pSVL (Pharmacia). However, any other plasmid or vector may be used as long as they are replicable and viable in the host.

Promoter regions can be selected from any desired gene using CAT (chloramphenicol transferass) vectors or other vectors with selectable markers. Two appropriate vectors are pKK232-8 and pCM7. Particular named bacterial promoters include lacI, lacZ, T3, T7, gpt, lambda $P_R$, $P_L$ and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art.

In a further embodiment, the present invention relates to host cells containing the above-described constructs. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, or electroporation (Davis, L., Dibner, M., Battey, I., Basic Methods in Molecular Biology, (1986)).

The constructs in host cells can be used in a conventional manner to produce the gene product encoded by the recombinant sequence. Alternatively, the polypeptides of the invention can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al., Molecular Cloning: A Laboratory Manual, Second Edition, Cold Spring Harbor, N.Y., (1989), the disclosure of which is hereby incorporated by reference.

Transcription of the DNA encoding the polypeptides of the present invention by higher eukaryotes is increased by inserting an enhancer sequence into the vector. Enhancers are cis-acting elements of DNA, usually about from 10 to 300 bp that act on a promoter to increase its transcription. Examples include the SV40 enhancer on the late side of the replication origin bp 100 to 270, a cytomegalovirus early promoter enhancer, the polyoma enhancer on the late side of the replication origin, and adenovirus enhancers.

Generally, recombinant expression vectors will include origins of replication and selectable markers permitting transformation of the host cell, e.g., the ampicillin resistance gene of E. coli and S. cerevisiae TRP1 gene, and a promoter derived from a highly-expressed gene to direct transcription of a downstream structural sequence. Such promoters can be derived from operons encoding glycolytic enzymes such as 3-phosphoglycerate kinase (PGK), α-factor, acid phosphatase, or heat shock proteins, among others. The heterologous structural sequence is assembled in appropriate phase with translation initiation and termination sequences. Optionally, the heterologous sequence can encode a fusion protein including an N-terminal identification peptide imparting desired characteristics, e.g., stabilization or simplified purification of expressed recombinant product.

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include E. coli, Bacillus subtilis, Salmonella typhimurium and various species within the genera Pseudomonas, Streptomyces, and Staphylococcus, although others may also be employed as a matter of choice.

As a representative but nonlimiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and GEM1 (Promega Biotec, Madison, Wis., USA). These pBR322 "backbone" sections are combined with an appropriate promoter and the structural sequence to be expressed.

Following transformation of a suitable host strain and growth of the host strain to an appropriate cell density, the selected promoter is induced by appropriate means (e.g., temperature shift or chemical induction) and cells are cultured for an additional period.

Cells are typically harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents, such methods are well known to those skilled in the art.

Various mammalian cell culture systems can also be employed to express recombinant protein. Examples of mammalian expression systems include the COS-7 lines of monkey kidney fibroblasts, described by Gluzman, Cell, 23:175 (1981), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 splice, and polyadenylation sites may be used to provide the required nontranscribed genetic elements.

The polypeptide can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the mature protein. Finally, high performance liquid chromatography (HPLC) can be employed for final purification steps.

The polypeptides of the present invention may be a naturally purified product, or a product of chemical synthetic procedures, or produced by recombinant techniques from a prokaryotic or eukaryotic host (for example, by bacterial, yeast, higher plant, insect and mammalian cells in culture). Depending upon the host employed in a recombinant production procedure, the polypeptides of the present invention may be glycosylated or may be non-glycosylated. Polypeptides of the invention may also include an initial methionine amino acid residue.

The oxalyl-CoA decarboxylase polypeptide of the present invention may be employed to prevent urinary stone formation by reducing the plasma or urinary levels of the oxalate ion.

The oxalyl-CoA decarboxylase polypeptide of the present invention may also be employed to treat or prevent hyperoxaluria. Hyperoxaluria is characterized by either abnormal synthesis or hyper-absorption of oxalate which can be prevented by degrading the oxalate ions and the prevention of this disorder.

The polypeptides of the present invention may be employed in combination with a suitable pharmaceutical carrier. Such compositions comprise a therapeutically effective amount of the polypeptide, and a pharmaceutically acceptable carrier or excipient. Such a carrier includes but is not limited to saline, buffered saline, dextrose, water, glycerol, ethanol, and combinations thereof. The formulation should suit the mode of administration.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the polypeptides of the present invention may be employed in conjunction with other therapeutic compounds.

The pharmaceutical compositions may be administered in a convenient manner such as by the topical, intravenous, intraperitoneal, intramuscular, subcutaneous, intranasal or intradermal routes. Oxalyl-CoA decarboxylase is administered in an amount which is effective for treating and/or prophylaxis of the specific indication. In general, the oxalyl-CoA decarboxylase will be administered in an amount of at least about 10 µg/kg bodyweight and in most cases will be administered in amounts not in excess of about 8 mg/Kg body weight per day. In most cases, the dosage is from about 10 µg/kg to about 1 mg/kg bodyweight daily, taking into account the routes of administration, symptoms, etc.

The polynucleotides and polypeptides of the present invention may be employed as research reagents and materials for discovery of treatments and diagnostics to human disease.

The Oxalyl-CoA decarboxylase polypeptides may also be employed in accordance with the present invention by expression of such polypeptides in vivo, which is often referred to as "gene therapy."

Thus, for example, cells from a patient may be engineered with a polynucleotide (DNA or RNA) encoding a polypeptide ex vivo, with the engineered cells then being provided to a patient to be treated with the polypeptide. Such methods are well-known in the art and are apparent from the teachings herein. For example, cells may be engineered by the use of a retroviral plasmid vector containing RNA encoding a polypeptide of the present invention.

Similarly, cells may be engineered in vivo for expression of a polypeptide in vivo by, for example, procedures known in the art. For example, a packaging cell is transduced with a retroviral plasmid vector containing RNA encoding a polypeptide of the present invention such that the packaging cell now produces infectious viral particles containing the gene of interest. These producer cells may be administered to a patient for engineering cells in vivo and expression of the polypeptide in vivo. These and other methods for administering a polypeptide of the present invention by such method should be apparent to those skilled in the art from the teachings of the present invention.

Retroviruses from which the retroviral plasmid vectors hereinabove mentioned may be derived include, but are not limited to, Moloney Murine Leukemia Virus, spleen necrosis virus, retroviruses such as Rous Sarcoma Virus, Harvey Sarcoma Virus, avian leukosis virus, gibbon ape leukemia virus, human immunodeficiency virus, adenovirus, Myeloproliferative Sarcoma Virus, and mammary tumor virus. In one embodiment, the retroviral plasmid vector is derived from Moloney Murine Leukemia Virus.

The vector includes one or more promoters. Suitable promoters which may be employed include, but are not limited to, the retroviral LTR; the SV40 promoter; and the human cytomegalovirus (CMV) promoter described in Miller, et al., *Biotechniques*, Vol. 7, No. 9, 980–990 (1989), or any other promoter (e.g., cellular promoters such as eukaryotic cellular promoters including, but not limited to, the histone, pol III, and β-actin promoters). Other viral promoters which may be employed include, but are not limited to, adenovirus promoters, thymidine kinase (TK) promoters, and B19 parvovirus promoters. The selection of a suitable promoter will be apparent to those skilled in the art from the teachings contained herein.

The nucleic acid sequence encoding the polypeptide of the present invention is under the control of a suitable promoter. Suitable promoters which may be employed include, but are not limited to, adenoviral promoters, such as the adenoviral major late promoter; or hetorologous promoters, such as the cytomegalovirus (CMV) promoter; the respiratory syncytial virus (RSV) promoter; inducible promoters, such as the MMT promoter, the metallothionein promoter; heat shock promoters; the albumin promoter; the ApoAI promoter; human globin promoters; viral thymidine kinase promoters, such as the Herpes Simplex thymidine kinase promoter; retroviral LTRs (including the modified retroviral LTRs hereinabove described); the β-actin promoter; and human growth hormone promoters. The promoter also may be the native promoter which controls the gene encoding the polypeptide.

The retroviral plasmid vector is employed to transduce packaging cell lines to form producer cell lines. Examples of packaging cells which may be transfected include, but are not limited to, the PE501, PA317, ψ-2, ψ-AM, PA12, T19-14X, VT-19-17-H2, ψCRE, ψCRIP, GP+E-86, GP+envAm12, and DAN cell lines as described in Miller, *Human Gene Therapy*, Vol. 1, pgs. 5–14 (1990), which is incorporated herein by reference in its entirety. The vector may transduce the packaging cells through any means known in the art. Such means include, but are not limited to, electroporation, the use of liposomes, and CaPO$_4$ precipitation. In one alternative, the retroviral plasmid vector may be encapsulated into a liposome, or coupled to a lipid, and then administered to a host.

The producer cell line generates infectious retroviral vector particles which include the nucleic acid sequence(s) encoding the polypeptides. Such retroviral vector particles then may be employed, to transduce eukaryotic cells, either in vitro or in vivo. The transduced eukaryotic cells will express the nucleic acid sequence(s) encoding the polypeptide. Eukaryotic cells which may be transduced include, but are not limited to, embryonic stem cells, embryonic carcinoma cells, as well as hematopoietic stem cells, hepatocytes, fibroblasts, myoblasts, keratinocytes, endothelial cells, and bronchial epithelial cells.

This invention is also related to the use of the gene of the present invention as a diagnostic. Detection of a mutated form of the gene will allow a diagnosis of a disease or a susceptibility to a disease which results from underexpression for example, hyperoxaluria.

Individuals carrying mutations in the human oxalyl-CoA decarboxylase gene may be detected at the DNA level by a variety of techniques. Nucleic acids for diagnosis may be obtained from a patient's cells, including but not limited to blood, urine, saliva, tissue biopsy and autopsy material. The genomic DNA may be used directly for detection or may be amplified enzymatically by using PCR (Saiki et al., Nature, 324:163–166 (1986)) prior to analysis. RNA or cDNA may also be used for the same purpose. As an example, PCR primers complementary to the nucleic acid encoding the polypeptide of the present invention can be used to identify and analyze mutations. For example, deletions and insertions can be detected by a change in size of the amplified product in comparison to the normal genotype. Point mutations can be identified by hybridizing amplified DNA to radiolabeled oxalyl-CoA decarboxylase RNA or alternatively, radiolabeled oxalyl-CoA decarboxylase antisense DNA sequences. Perfectly matched sequences can be distinguished from mismatched duplexes by RNase A digestion or by differences in melting temperatures.

Sequence differences between the reference gene and genes having mutations may be revealed by the direct DNA sequencing method. In addition, cloned DNA segments may be employed as probes to detect specific DNA segments. The sensitivity of this method is greatly enhanced when combined with PCR. For example, a sequencing primer is used with double-stranded PCR product or a single-stranded template molecule generated by a modified PCR. The sequence determination is performed by conventional procedures with radiolabeled nucleotide or by automatic sequencing procedures with fluorescent-tags.

Genetic testing based on DNA sequence differences may be achieved by detection of alteration in electrophoretic mobility of DNA fragments in gels with or without denaturing agents. Small sequence deletions and insertions can be visualized by high resolution gel electrophoresis. DNA fragments of different sequences may be distinguished on denaturing formamide gradient gels in which the mobilities of different DNA fragments are retarded in the gel at different positions according to their specific melting or partial melting temperatures (see, e.g., Myers et al., Science, 230:1242 (1985)).

Sequence changes at specific locations may also be revealed by nuclease protection assays, such as RNase and S1 protection or the chemical cleavage method (e.g., Cotton et al., PNAS, USA, 85:4397–4401 (1985)).

Thus, the detection of a specific DNA sequence may be achieved by methods such as hybridization, RNase protection, chemical cleavage, direct DNA sequencing or the use of restriction enzymes, (e.g., Restriction Fragment Length Polymorphisms (RFLP)) and Southern blotting of genomic DNA.

In addition to more conventional gel-electrophoresis and DNA sequencing, mutations can also be detected by in situ analysis.

The present invention also relates to a diagnostic assay for detecting altered levels of oxalyl-CoA decarboxylase protein in various tissues since an over-expression of the proteins compared to normal control tissue samples can detect the presence of oxalyl-CoA decarboxylase. Assays used to detect levels of oxalyl-CoA decarboxylase protein in a sample derived from a host are well-known to those of skill in the art and include radioimmunoassays, competitive-binding assays, Western Blot analysis and preferably an ELISA assay. An ELISA assay initially comprises preparing an antibody specific to the oxalyl-coA decarboxylase antigen, preferably a monoclonal antibody. In addition a reporter antibody is prepared against the monoclonal antibody. To the reporter antibody is attached a detectable reagent such as radioactivity, fluorescence or in this example a horseradish peroxidase enzyme. A sample is now removed from a host and incubated on a solid support, e.g. a polystyrene dish, that binds the proteins in the sample. Any free protein binding sites on the dish are then covered by incubating with a nonspecific protein such as bovine serum albumin. Next, the monoclonal antibody is incubated in the dish during which time the monoclonal antibodies attach to any oxalyl-CoA decarboxylase protein attached to the polystyrene dish. All unbound monoclonal antibody is washed out with buffer. The reporter antibody linked to horseradish peroxidase is now placed in the dish resulting in binding of the reporter antibody to any monoclonal antibody bound to the polypeptide of the present invention. Unattached reporter antibody is then washed out. Peroxidase substrates are then added to the dish and the amount of color developed in a given time period is a measurement of the amount of protein present in a given volume of patient sample when compared against a standard curve.

A competition assay may be employed wherein antibodies specific to oxalyl-CoA decarboxylase are attached to a solid support and labeled oxalyl-CoA decarboxylase and a sample derived from the host are passed over the solid support and the amount of label detected attached to the solid support can be correlated to a quantity of oxalyl-CoA decarboxylase in the sample.

The present invention will be further described with reference to the following examples, however, it is to be understood that the present invention is not limited to such examples. All parts or amounts, unless otherwise specified, are by weight.

In order to facilitate understanding of the following examples certain frequently occurring methods and/or terms will be described.

"Plasmids" are designated by a lower case p preceded and/or followed by capital letters and/or numbers. The starting plasmids herein are either commercially available, publicly available on an unrestricted basis, or can be constructed from available plasmids in accord with published procedures. In addition, equivalent plasmids to those described are known in the art and will be apparent to the ordinarily skilled artisan.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 µg of plasmid or DNA fragment is used with about 2 units of enzyme in about 20 µl of buffer solution. For the purpose of isolating DNA fragments for plasmid construction, typically 5 to 50 µg of DNA are digested with 20 to 250 units of enzyme in a larger volume. Appropriate buffers and substrate amounts for particular restriction enzymes are specified by the manufacturer. Incubation times of about 1 hour at 37° C. are ordinarily used, but may vary in accordance with the supplier's instructions. After digestion the reaction is electrophoresed directly on a polyacrylamide gel to isolate the desired fragment.

Size separation of the cleaved fragments is performed using 8 percent polyacrylamide gel described by Goeddel, D. et al., Nucleic Acids Res., 8:4057 (1980).

"Oligonucleotides" refers to either a single stranded polydeoxynucleotide or two complementary polydeoxynucleotide strands which may be chemically synthesized. Such synthetic oligonucleotides have no 5' phosphate and thus will not ligate to another oligonucleotide without adding a phosphate with an ATP in the presence of a kinase. A synthetic oligonucleotide will ligate to a fragment that has not been dephosphorylated.

"Ligation" refers to the process of forming phosphodiester bonds between two double stranded nucleic acid fragments (Maniatis, T., et al., Id., p. 146). Unless otherwise provided, ligation may be accomplished using known buffers and conditions with 10 units to T4 DNA ligase ("ligase") per 0.5 µg of approximately equimolar amounts of the DNA fragments to be ligated.

Unless otherwise stated, transformation was performed as described in the method of Graham, F. and Van der Eb, A., Virology, 52:456–457 (1973).

EXAMPLE 1

Bacterial Expression and Purification of Oxalyl-CoA decarboxylase

The DNA sequence encoding for oxalyl-CoA decarboxylase, ATCC #75715, is initially amplified using PCR oligonucleotide primers corresponding to the 5' and 3' sequences of the processed oxalyl-CoA decarboxylase protein (minus the signal peptide sequence) and additional nucleotides corresponding to Nco I and Bgl II were added to the 5' and 3' sequences respectively. The primers used for generation of the PCR fragment will encode the OmpA leader sequence in addition to the restriction sites in the sequence encoding the human oxalyl-CoA decarboxylase. The 5' oligonucleotide primer has the sequence 5' GACTTCATGAAAAAGAC AGATATCGCAATTGCAGTG-GCACTGGCTGGTTTCGCTACCGTTGCG-CAAGCTGCTCCGGA CAGTAACTTCGCAGAG 3' (SEQ ID NO.:3) contains a BspH I restriction enzyme site followed by 21 nucleotides of the human oxalyl-CoA decarboxylase gene; the 3' sequence is 5' CAGTTCTAGA-CATATTAGAGCGGGTCAGCC 3' (SEQ ID NO:4) contains complementary sequences to Bgl II restriction enzyme site, a translation stop codon and the last 20 nucleotides of the human oxalyl-CoA decarboxylase coding sequence. The restriction enzyme sites correspond to the restriction enzyme sites on the bacterial expression vector pQE-60 (Qiagen, Inc. 9259 Eton Ave., Chatsworth, Calif. 91311). pQE-60 encodes antibiotic resistance (Amp$^r$), a bacterial origin of replication (ori), an IPTG-regulatable promoter operator (P/O), a ribosome binding site (RBS), a 6-His tag and restriction enzyme sites. pQE-60 was then digested with Nco I and Bgl II. The amplified sequences were ligated into PQE-60 and were inserted in frame with the sequence encoding for the histidine tag and the RBS. The ligation mixture was then used to transform E. colistrain M15/rep4 available from Qiagen under the trademark M15/rep 4. M15/rep4 contains multiple copies of the plasmid pREP4, which expresses the lacI repressor and also confers kanamycin resistance (Kan$^r$). Transformants are identified by their ability to grow on LB plates and ampicillin/kanamycin resistant colonies were selected. Plasmid DNA was isolated and confirmed by restriction analysis. Clones containing the desired constructs were grown overnight (O/N) in liquid culture in LB media supplemented with both Amp (100 ug/ml) and Kan (25 ug/ml). Tho O/N culture is used to inoculate a large culture at a ratio of 1:100 to 1:250. The cells were grown to an optical density 600 (O.D.$^{600}$) of between 0.4 and 0.6. IPTG (Isopropyl-B-D-thiogalacto pyranoside) was then added to a final concentration of 1 mM. IPTG induces by inactivating the lacI repressor, clearing the P/O leading to increased gene expression. Cells were grown an extra 3 to 4 hours. Cells were then harvested by centrifugation (20 mins at 6000 Xg). The cell pellet was solubilized in the chaotropic agent 6 Molar Guanidine HCl. After clarification, solubilized oxalyl-CoA decarboxylase was purified from this solution by chromatography on a Nickel-Chelate column under conditions that allow for tight binding by proteins containing the 6-His tag (Hochuli, E. et al., Genetic Engineering, Principles & Methods, 12:87–98 (1990). Protein renaturation out of GnHCl can be accomplished by several protocols (Jaenicke, R. and Rudolph, R., Protein Structure—A Practical Approach, IRL Press, New York (1990)). Oxalyl-CoA decarboxylase (95% pure) was eluted from the column in 6 molar guanidine HCl pH 5.0 and for the purpose of renaturation adjusted to 3 molar guanidine HCl, 100 mM sodium phosphate, 10 mmolar glutathione (reduced) and 2 mmolar glutathione (oxidized).

EXAMPLE 2

Expression of Human Oxalyl-CoA Decarboxylase by in vitro transcription and translation The in vitro transcription and translation of the oxalyl-CoA decarboxylase was carried out using the TNT Coupled Reticulocyte Lysate System (Promega, Madison, Wis.). The cDNA encoding for oxalyl-CoA decarboxylase was cloned directionally EcoRI to XhoI with the EcoRI site defining the 5' end of the gene and the XhoI site defining the 3' end of the gene. The gene was inserted in the T3 direction. T3 defines a bacteriophage RNA polymerase which recognizes a specific promoter, and transcribes the DNA into a mRNA. A rabbit reticulocyte lysate is supplemented with T3 RNA polymerase and directs the expression of proteins with a T3 promoter utilizing the T3 RNA polymerase to transcribe the message, and the reticulocyte lysate to translate the nascent RNA. By incorporating radioactive amino acids into the translated product, protein expression can be analyzed using SDS-polyacrylamide gel electrophoresis followed by autoradiography. More specifically, 1 µg of plasmid containing the oxalyl-CoA decarboxylase DNA was incubated at 30° C. for 1 hour with the reticulocyte lysate, T3 RNA polymerase and [$^{35}$S]-Methionine. After incubation, the translations were analyzed by SDS-PAGE and autoradiography. A prominent translation product was visible at ≈55 Kd.

EXAMPLE 3

Expression via Gene Therapy

Fibroblasts are obtained from a subject by skin biopsy. The resulting tissue is placed in tissue-culture medium and separated into small pieces. Small chunks of the tissue are placed on a wet surface of a tissue culture flask, approximately ten pieces are placed in each flask. The flask is turned upside down, closed tight and left at room temperature over night. After 24 hours at room temperature, the flask is inverted and the chunks of tissue remain fixed to the bottom of the flask and fresh media (e.g., Ham's F12 media, with 10% FBS, penicillin and streptomycin, is added. This is then incubated at 37° C. for approximately one week. At this time, fresh media is added and subsequently changed every several days. After an additional two weeks in culture, a monolayer of fibroblasts emerge. The monolayer is trypsinized and scaled into larger flasks.

pMV-7 (Kirschmeier, P. T. et al, DNA, 7:219-25 (1988) flanked by the long terminal repeats of the Moloney murine sarcoma virus, is digested with EcoRI and HindIII and subsequently treated with calf intestinal phosphatase. The linear vector is fractionated on agarose gel and purified, using glass beads.

The cDNA encoding a polypeptide of the present invention is amplified using PCR primers which correspond to the 5' and 3' end sequences respectively. The 5' primer containing an EcoRI site and the 3' primer further includes a HindIII site. Equal quantities of the Moloney murine sarcoma virus linear backbone and the amplified EcoRI and HindIII fragment are added together, in the presence of T4 DNA ligase.

The resulting mixture is maintained under conditions appropriate for ligation of the two fragments. The ligation mixture is used to transform bacteria HB101, which are then plated onto agar-containing kanamycin for the purpose of confirming that the vector had the gene of interest properly inserted.

The amphotropic pA317 or GP+am12 packaging cells are grown in tissue culture to confluent density in Dulbecco's Modified Eagles Medium (DMEM) with 10% calf serum (CS), penicillin and streptomycin. The MSV vector containing the gene is then added to the media and the packaging cells are transduced with the vector. The packaging cells now produce infectious viral particles containing the gene (the packaging cells are now referred to as producer cells).

Fresh media is added to the transduced producer cells, and subsequently, the media is harvested from a 10 cm plate of confluent producer cells. The spent media, containing the infectious viral particles, is filtered through a millipore filter to remove detached producer cells and this media is then used to infect fibroblast cells. Media is removed from a sub-confluent plate of fibroblasts and quickly replaced with the media from the producer cells. This media is removed and replaced with fresh media. If the titer of virus is high, then virtually all fibroblasts will be infected and no selection is required. If the titer is very low, then it is necessary to use a retroviral vector that has a selectable marker, such as neo or his.

The engineered fibroblasts are then injected into the host, either alone or after having been grown to confluence on cytodex 3 microcarrier beads. The fibroblasts now produce the protein product.

Numerous modifications and variations of the present invention are possible in light of the above teachings and, therefore, within the scope of the appended claims, the invention may be practiced otherwise than as particularly described.

What is claimed is:

1. An isolated polynucleotide comprising a polynucleotide member selected from the group consisting of:
   (a) a polynucleotide having a sequence with least 95% identity to a polynucleotide coding sequence encoding amino acids 2 to 578 of SEQ ID NO:2; and
   (b) the complement of the polynucleotide of (a).

2. The isolated polynucleotide of claim 1 wherein said member is the polynucleotide of (a).

3. The isolated polynucleotide of claim 1 wherein said member is the polynucleotide of (a) and the polynucleotide coding sequence encodes amino acids 1 to 578 of SEQ ID NO:2.

4. The isolated polynucleotide of claim 1 comprising a polynucleotide identical to a polynucleotide coding sequence encoding amino acids 2 to 578 of SEQ ID NO:2.

5. The isolated polynucleotide of claim 1, wherein the polynucleotide is DNA.

6. The isolated polynucleotide of claim 1 comprising a polynucleotide identical to a polynucleotide coding sequence encoding amino acids 1 to 578 of SEQ ID NO:2.

7. The isolated polynucleotide of claim 1, wherein said polynucleotide is RNA.

8. A method of making a recombinant vector comprising inserting the isolated polynucleotide of claim 2 into a vector, wherein said polynucleotide is DNA.

9. A recombinant vector comprising the polynucleotide of claim 2, wherein said polynucleotide is DNA.

10. A recombinant host cell transformed, transduced or transfected with the vector of claim 9, resulting in recombinant host cell that comprises said polynucleotide.

11. A method for producing a polypeptide comprising expressing from the recombinant cell of claim 10 the polypeptide encoded by said polynucleotide.

12. A process for producing a polypeptide comprising:
   expressing from a recombinant cell transformed, transduced, or transfected to contain the polynucleotide of claim 4, the polypeptide encoded by said polynucleotide.

13. A process for producing a polypeptide comprising:
   expressing from a recombinant cell transformed, transduced, or transfected to contain the polynucleotide of claim 6, the polypeptide encoded by said polynucleotide.

14. The isolated polynucleotide of claim 1 comprising nucleotides 13 to 1743 of SEQ ID NO:1.

15. The isolated polynucleotide of claim 1 comprising nucleotides 10 to 1743 of SEQ ID NO:1.

16. The isolated polynucleotide of claim 1 comprising the nucleotides of the sequence of SEQ ID NO:1.

17. An isolated polynucleotide comprising a polynucleotide member selected from the group consisting of:
   (a) a polynucleotide having a sequence with at least 95% identify to the portion of a polynucleotide sequence encoding the same mature polypeptide encoded by the human cDNA in ATCC Deposit No. 75715; and
   (b) the complement of the polynucleotide of (a).

18. The isolated polynucleotide of claim 17, wherein the member is the polynucleotide of (a).

19. The isolated polynucleotide of claim 17, wherein said polynucleotide comprises DNA identical to the coding portion of the human cDNA in ATCC Deposit No. 75715 which encodes a mature polypeptide.

20. A method of detecting a difference in nucleotide sequence between the polynucleotide of claim 2 and a polynucleotide encoding human oxalyl-CoA decarboxylase from a patient comprising, obtaining a nucleic acid sample from a patient and analyzing said nucleic acid sample to detect one or more sequence differences.

21. A method of detecting a difference in nucleotide sequence between the polynucleotide of claim 4 and a polynucleotide encoding human oxalyl-CoA decarboxylase from a patient comprising, obtaining a nucleic acid sample from a patient and analyzing said nucleic acid sample to detect one or more sequence differences.

22. A method of detecting a difference in nucleotide sequence between the polynucleotide of claim 6 and a polynucleotide encoding human oxalyl-CoA decarboxylase from a patient comprising, obtaining a nucleic acid sample from a patient and analyzing said nucleic acid sample to detect one or more sequence differences.

* * * * *

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 1882 BASE PAIRS
        ( B ) TYPE: NUCLEIC ACID
        ( C ) STRANDEDNESS: SINGLE
        ( D ) TOPOLOGY: LINEAR ( i i ) MOLECULE TYPE: cDNA ( x i ) SEQUENCE DESCRIPTION: SEQ ID NO:1:

```
CGGTGGAAGA  TGCCGGACAG  TAACTTCGCA  GAGCGCAGCG  AGGAGCAGGT  GTCTGGTGCT      60

AAAGTCATCG  CTCAGGCCCT  GAAAACGCAA  GATGTGGAGT  ACATATTTGG  CATCGTAGGC     120

ATCCCAGTGA  CCGAAATCGC  CATTGCTGCC  CAGCAGCTAG  GCATCAAGTA  CATCGGGATG     180

AGGAATGAGC  AAGCGGCTTG  TTATGCTGCC  TCCGCGATTG  GATATCTGAC  AAGCAGGCCA     240

GGAGTCTGCC  TTGTTGTTTC  TGGCCCAGGT  CTCATCCATG  CCTTGGGCGG  TATGGCAAAT     300

GCAAACATGA  ACTGCTGGCC  CTTGCTTGTG  ATTGGTGGTT  CCTCTGAAAG  AAACCAAGAA     360

ACAATGGGAG  CTTTCCAGGA  GTTTCCTCAG  GTTGAAGCTT  GTAGATTATA  TACCAAGTTC     420

TCTGCCCGCC  CAAGCAGCAT  AGAAGCTATT  CCTTTTGTTA  TTGAAAAGGC  AGTGAGAAGC     480
```

-continued

```
AGTATCTATG GTCGTCCAGG TGCTTGCTAT GTTGACATAC CAGCAGATTT TGTGAACCTT    540
CAGGTGAATG TGAATTCTAT AAAGTACATG GAACGCTGCA TGTCACCTCC TATTAGCATG    600
GCAGAAACCT CTGCTGTGTG CACGGCGGCT TCTGTTATTA GGAATGCCAA ACAACCCCTT    660
CTTATCATCG GGAAAGGTGC TGCTTACGCT CATGCAGAAG AGAGTATCAA GAAATTGGTG    720
GAGCAATATA AACTGCCATT TTTGCCCACC CCTATGGGGA AGGGTGTTGT CCCTGACAAT    780
CATCCATACT GTGTAGGTGC AGCCAGATCC AGGGCTTTGC AATTTGCTGA TGTAATTGTG    840
TTATTTGGTG CCAGACTAAA TTGGATTTTA CATTTTGGAC TGCCTCCAAG ATATCAGCCA    900
GATGTGAAGT TTATCCAGGT TGATATCTGT GCAGAAGAAT GGGGAATAA TGTAAAGCCC     960
GCTGTTACTT TGCTAGGAAA CATACATGCT GTCACTAAGC AGCTTTTAGA GGAACTTGAT   1020
AAAACACCAT GGCAGTATCC TCCAGAGAGC AAGTGGTGGA AAACTCTGAG AGAAAAAATG   1080
AAGAGCAATG AAGCTGCATC CAAGGAACTA GCTTCTAAAA AATCCCTGCC TATGAATTAT   1140
TACACAGTAT CTACCATGT TCAAGAACAA CTACCTAGAG ACTGTTTCGT GGTAAGTGAA    1200
GGAGCAAATA CTATGGACAT TGGACGGACT GTGCTTCAGA ACTACCTTCC TCGTCACAGG   1260
CTTGATGCTG GTACTTTCGG AACAATGGGA GTTGGTTTGG GATTTGCTAT TGCAGCTGCC   1320
GTGGTGGCTA AAGATAGAAG CCCTGGGCAA TGGATCATCT GTGTGGAAGG AGACAGTGCA   1380
TTTGGGTTTT CTGGCATGGA GGTAGAAACC ATCTGCAGGT ACAACTTGCC AATCATACTG   1440
TTGGTAGTGA ATAACAATGG AATTTACCAA GGTTTTGATA CAGATACTTG GAAAGAAATG   1500
TTAAAATTTC AAGATGCTAC TGCAGTGGTC CCTCCAATGT GTTTGCTGCC AAATTCACAT   1560
TATGAGCAAG TCATGACTGC ATTTGGAGGC AAAGGGTGTT TTGTACAAAC ACCAGAAGAA   1620
CTCCAAAAAT CCCTGAGGCA GAGCCTAGCA GACACAACTA AACCTTCTCT TATCAACATC   1680
ATGATTGAGC CACAAGCCAC ACGGAAGGCC CAGGATTTTC ATTGGCTGAC CCGCTCTAAT   1740
ATGTAAATAA AGACGCCAGT TGGTGGTCTT GAGTTTCTC TTTCTTGCAA GATGAAATTT    1800
TATTTTCACA GCAAAATTAC TCTACTGTTA AAATTGTGCA AATAAAATA AACATTTAAC    1860
AATGAAAAAA AAAAAAAAA AA                                             1882
```

( 2 ) INFORMATION FOR SEQ ID NO:2:

( i ) SEQUENCE CHARACTERISTICS:
        ( A ) LENGTH: 578 AMINO ACIDS
        ( B ) TYPE: AMINO ACID
        ( C ) STRANDEDNESS:
        ( D ) TOPOLOGY: LINEAR ( i i ) MOLECULE TYPE: PROTEIN ( x i ) SEQUENCE DESCRIPTION: SEQ ID NO:2:

```
Met Pro Asp Ser Asn Phe Ala Glu Arg Ser Glu Glu Gln Val Ser
                  5                  10                  15

Gly Ala Lys Val Ile Ala Gln Ala Leu Lys Thr Gln Asp Val Glu
                 20                  25                  30

Tyr Ile Phe Gly Ile Val Gly Ile Pro Val Thr Glu Ile Ala Ile
                 35                  40                  45

Ala Ala Gln Gln Leu Gly Ile Lys Tyr Ile Gly Met Arg Asn Glu
                 50                  55                  60

Gln Ala Ala Cys Tyr Ala Ala Ser Ala Ile Gly Tyr Leu Thr Ser
                 65                  70                  75

Arg Pro Gly Val Cys Leu Val Val Ser Gly Pro Gly Leu Ile His
                 80                  85                  90
```

| | | | | | | | | | | | | | |
|---|---|---|---|---|---|---|---|---|---|---|---|---|---|
|Ala|Leu|Gly|Gly|Met 95|Ala|Asn|Ala|Asn|Met 100|Asn|Cys|Trp|Pro|Leu 105|
|Leu|Val|Ile|Gly|Gly 110|Ser|Ser|Glu|Arg|Asn 115|Gln|Glu|Thr|Met|Gly 120|
|Ala|Phe|Gln|Glu|Phe 125|Pro|Gln|Val|Glu|Ala 130|Cys|Arg|Leu|Tyr|Thr 135|
|Lys|Phe|Ser|Ala|Arg 140|Pro|Ser|Ser|Ile|Glu 145|Ala|Ile|Pro|Phe|Val 150|
|Ile|Glu|Lys|Ala|Val 155|Arg|Ser|Ser|Ile|Tyr 160|Gly|Arg|Pro|Gly|Ala 165|
|Cys|Tyr|Val|Asp|Ile 170|Pro|Ala|Asp|Phe|Val 175|Asn|Leu|Gln|Val|Asn 180|
|Val|Asn|Ser|Ile|Lys 185|Tyr|Met|Glu|Arg|Cys 190|Met|Ser|Pro|Pro|Ile 195|
|Ser|Met|Ala|Glu|Thr 200|Ser|Ala|Val|Cys|Thr 205|Ala|Ala|Ser|Val|Ile 210|
|Arg|Asn|Ala|Lys|Gln 215|Pro|Leu|Leu|Ile|Ile 220|Gly|Lys|Gly|Ala|Ala 225|
|Tyr|Ala|His|Ala|Glu 230|Glu|Ser|Ile|Lys|Lys 235|Leu|Val|Glu|Gln|Tyr 240|
|Lys|Leu|Pro|Phe|Leu 245|Pro|Thr|Pro|Met|Gly 250|Lys|Gly|Val|Val|Pro 255|
|Asp|Asn|His|Pro|Tyr 260|Cys|Val|Gly|Ala|Ala 265|Arg|Ser|Arg|Ala|Leu 270|
|Gln|Phe|Ala|Asp|Val 275|Ile|Val|Leu|Phe|Gly 280|Ala|Arg|Leu|Asn|Trp 285|
|Ile|Leu|His|Phe|Gly 290|Leu|Pro|Pro|Arg|Tyr 295|Gln|Pro|Asp|Val|Lys 300|
|Phe|Ile|Gln|Val|Asp 305|Ile|Cys|Ala|Glu|Glu 310|Leu|Gly|Asn|Asn|Val 315|
|Lys|Pro|Ala|Val|Thr 320|Leu|Leu|Gly|Asn|Ile 325|His|Ala|Val|Thr|Lys 330|
|Gln|Leu|Leu|Glu|Glu 335|Leu|Asp|Lys|Thr|Pro 340|Trp|Gln|Tyr|Pro|Pro 345|
|Glu|Ser|Lys|Trp|Trp 350|Lys|Thr|Leu|Arg|Glu 355|Lys|Met|Lys|Ser|Asn 360|
|Glu|Ala|Ala|Ser|Lys 365|Glu|Leu|Ala|Ser|Lys 370|Lys|Ser|Leu|Pro|Met 375|
|Asn|Tyr|Tyr|Thr|Val 380|Phe|Tyr|His|Val|Gln 385|Glu|Gln|Leu|Pro|Arg 390|
|Asp|Cys|Phe|Val|Val 395|Ser|Glu|Gly|Ala|Asn 400|Thr|Met|Asp|Ile|Gly 405|
|Arg|Thr|Val|Leu|Gln 410|Asn|Tyr|Leu|Pro|Arg 415|His|Arg|Leu|Asp|Ala 420|
|Gly|Thr|Phe|Gly|Thr 425|Met|Gly|Val|Gly|Leu 430|Gly|Phe|Ala|Ile|Ala 435|
|Ala|Ala|Val|Val|Ala 440|Lys|Asp|Arg|Ser|Pro 445|Gly|Gln|Trp|Ile|Ile 450|
|Cys|Val|Glu|Gly|Asp 455|Ser|Ala|Phe|Gly|Phe 460|Ser|Gly|Met|Glu|Val 465|
|Glu|Thr|Ile|Cys|Arg 470|Tyr|Asn|Leu|Pro|Ile 475|Ile|Leu|Leu|Val|Val 480|
|Asn|Asn|Asn|Gly|Ile 485|Tyr|Gln|Gly|Phe|Asp 490|Thr|Asp|Thr|Trp|Lys 495|

| | | | | | | | | | | | | |
|---|---|---|---|---|---|---|---|---|---|---|---|---|
| Glu | Met | Leu | Lys | Phe 500 | Gln | Asp | Ala | Thr | Ala 505 | Val | Val | Pro | Pro | Met 510 |
| Cys | Leu | Leu | Pro | Asn 515 | Ser | His | Tyr | Glu | Gln 520 | Val | Met | Thr | Ala | Phe 525 |
| Gly | Gly | Lys | Gly | Tyr 530 | Phe | Val | Gln | Thr | Pro 535 | Glu | Glu | Leu | Gln | Lys 540 |
| Ser | Leu | Arg | Gln | Ser 545 | Leu | Ala | Asp | Thr | Thr 550 | Lys | Pro | Ser | Leu | Ile 555 |
| Asn | Ile | Met | Ile | Glu 560 | Pro | Gln | Ala | Thr | Arg 565 | Lys | Ala | Gln | Asp | Phe 570 |
| His | Trp | Leu | Thr | Arg 575 | Ser | Asn | Met | | | | | | |

( 2 ) INFORMATION FOR SEQ ID NO:3:

( i ) SEQUENCE CHARACTERISTICS:
        ( A ) LENGTH: 93 BASE PAIRS
        ( B ) TYPE: NUCLEIC ACID
        ( C ) STRANDEDNESS: SINGLE
        ( D ) TOPOLOGY: LINEAR ( i i ) MOLECULE TYPE: Oligonucleotide ( x i ) SEQUENCE DESCRIPTION: SEQ ID NO:3:

```
GACTTCATGA AAAAGACAGA TATCGCAATT GCAGTGGCAC TGGCTGGTTT CGCTACCGTT       60

GCGCAAGCTG CTCCGGACAG TAACTTCGCA GAG                                    93
```

( 2 ) INFORMATION FOR SEQ ID NO:4:

( i ) SEQUENCE CHARACTERISTICS:
        ( A ) LENGTH: 30 BASE PAIRS
        ( B ) TYPE: NUCLEIC ACID
        ( C ) STRANDEDNESS: SINGLE
        ( D ) TOPOLOGY: LINEAR ( i i ) MOLECULE TYPE: Oligonucleotide ( x i ) SEQUENCE DESCRIPTION: SEQ ID NO:4:

```
CAGTTCTAGA CATATTAGAG CGGGTCAGCC                                        30
```